United States Patent [19]

Kawakami

[11] Patent Number: 5,171,720
[45] Date of Patent: Dec. 15, 1992

[54] POROUS CERAMIC SINTER AND PROCESS FOR PRODUCING SAME

[75] Inventor: Michiko Kawakami, Tokyo, Japan

[73] Assignee: Asahi Kogaku Kogyo K.K., Tokyo, Japan

[21] Appl. No.: 409,917

[22] Filed: Sep. 20, 1989

[30] Foreign Application Priority Data

Sep. 20, 1988 [JP] Japan ................. 63-235520

[51] Int. Cl.⁵ ................................ C04B 38/00
[52] U.S. Cl. .............................. 501/80; 501/81; 501/82; 501/83
[58] Field of Search ............... 501/80, 81, 82, 83, 501/84, 85

[56] References Cited

U.S. PATENT DOCUMENTS

| 4,004,933 | 1/1977 | Ravault | 501/81 |
| 4,195,366 | 4/1980 | Jarcho et al. | 501/1 |
| 4,312,821 | 1/1982 | Jarcho et al. | 264/43 |
| 4,551,295 | 11/1985 | Gardner et al. | 264/60 |
| 4,629,464 | 12/1986 | Takata et al. | 623/16 |
| 4,654,314 | 3/1987 | Takagi et al. | 501/80 |
| 4,657,880 | 4/1987 | Lachman et al. | 502/263 |
| 4,812,424 | 3/1989 | Helferich et al. | 501/125 |
| 4,846,838 | 7/1989 | Takai et al. | 501/81 |
| 4,846,906 | 7/1989 | Helferich et al. | 264/60 |
| 4,871,495 | 10/1989 | Helferich et al. | 501/84 |
| 4,889,670 | 12/1989 | Gurak et al. | 264/64 |

FOREIGN PATENT DOCUMENTS

| 20068360 | 1/1983 | European Pat. Off. . |
| 0200528 | 11/1986 | European Pat. Off. . |
| 20264268 | 4/1988 | European Pat. Off. . |
| 2145710 | 3/1985 | Fed. Rep. of Germany . |
| 54-50194 | 4/1979 | Japan . |

OTHER PUBLICATIONS

English translation of relevant parts of JP-A-54-50194.

Primary Examiner—Mark L. Bell
Assistant Examiner—Susan Hollenbeck
Attorney, Agent, or Firm—Sughrue, Mion, Zinn, Macpeak & Seas

[57] ABSTRACT

A porous ceramic sinter and a process for producing the same are disclosed, which sinter has macropores with a pore size of from 20 to 2,000 μm and three-dimensionally communicating pores that are made of interstices between secondary particles.

12 Claims, 2 Drawing Sheets

POROUS CERAMIC SINTER AND PROCESS FOR PRODUCING SAME

FIELD OF THE INVENTION

The present invention relates to a porous ceramic sinter and dried body, and processes for producing them.

BACKGROUND OF THE INVENTION

It is known to produce porous ceramics by wet processes such as a foaming method and a method involving the use of heat decomposable beads.

In the foaming method, a foaming agent such as an aqueous solution of hydrogen peroxide is added to a slurry of starting ceramic powder, which is then dried and foamed to make a porous ceramic material. A problem with this method is the difficulty in controlling the pore size and the porosity.

In the other wet process which involves the use of heat decomposable beads, a slurry of a starting ceramic powder is mixed and kneaded with beads of an organic polymer, and after the mixture is shaped, it is heated to burn away the organic polymer and produce a porous ceramic material. This method, however, suffers the disadvantage that the beads do not shrink upon drying so as to develop distortion of the dried product. Further, the use of beads in a large amount leads to some difficulty in the degreasing step (i.e., the step of removing the heat decomposable substance).

SUMMARY OF THE INVENTION

One object, therefore, of the present invention is to provide a porous ceramic sinter having both macropores of a uniform size and micropores in communication with each other to establish a three-dimensional network, which sinter exhibits high strength and good cutting properties.

Another object of the present invention is to provide a porous dried body having a strength that withstands subsequent cutting operations, which is capable of being immediately subjected to cutting without calcination.

Still another object of the present invention is to provide a process of producing such a porous ceramic sinter or dried body without causing cracking or other problems in the drying step used.

The above and other objects and effects of the present invention will be more apparent from the following description.

The present invention provides a porous ceramic sinter having macropores with a pore size of from 20 to 2,000 μm and three-dimensionally communicating micropores that are made of interstices between secondary particles.

The present invention also provides a porous ceramic dried body having macropores with a pore size of from 20 to 2,000 μm comprising ceramic particles bound with a high molecular weight material.

The present invention also provides a process for producing a porous ceramic dried body which comprises: casting a slurry comprising a ceramic powder, a high molecular weight material and air bubbles into a mold; increasing the viscosity of the cast product or allowing the cast product to gel while maintaining the air bubbles; and drying the viscous or gelled cast product.

The sinter of the present invention can be produced by firing the dried body of the present invention.

DETAILED DESCRIPTION OF THE INVENTION

Figure 1:
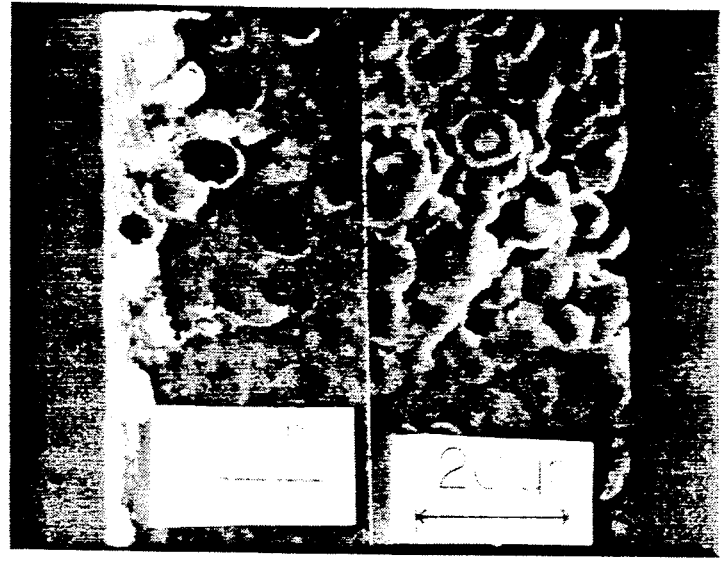
FIGS. 1 and 2 show micrographs of the sinters MC1 and MC2 obtained in Example 1, respectively.

In the process for producing a porous ceramic dried body or sinter of the present invention, a method for producing the slurry, which comprises a ceramic powder, a high molecular weight material and air bubbles, (such as the order of mixing, a method for entraining air bubbles, etc.) is not limited.

In one embodiment of the present invention, the process for producing the porous ceramic sinter of the present invention comprises: mixing a ceramic powder with a solution or fluid gel of a high molecular weight material into which air bubbles have been entrained by stirring to yield a slurry; casting the resulting slurry into a mold; increasing the viscosity of the cast product or allowing the cast product to gel while maintaining the air bubbles; drying the viscous or gelled product; and firing the dried body.

In another embodiment of the present invention, the process for producing the porous ceramic sinter of the present invention comprises: mixing a ceramic powder with a solution or fluid gel of a high-molecular weight material; stirring the mixture to entrain air bubbles in the mixture and to thereby yield a slurry; casting the resulting slurry into a mold; increasing the viscosity of the cast product or allowing the cast product to gel while maintaining the air bubbles; drying the viscous or gelled cast product; and firing the dried body.

In still another embodiment of the present invention, the process for producing the porous ceramic sinter of the present invention comprises: mixing a ceramic powder with a high-molecular weight material; mixing the mixture with a dispersion medium; stirring the mixture to entrain air bubbles in the mixture to thereby yield a slurry; casting the resulting slurry into a mold; increasing the viscosity of the cast product or allowing the cast product to gel while maintaining the air bubbles; drying the viscous or gelled cast product; and firing the dried body.

The ceramic powder used in the present invention as a starting material may be prepared by any conventional methods.

The ceramic powder used in the present invention is preferably spherical secondary particles having an average particle size of from about 10 to 100 μm. More preferably, these spherical secondary particles are pulverized by jet milling or some other suitable method to such an extent that their surfaces are scraped to produce from 1 to 30 wt % of fine particles having a size of from about 0.1 to 2 μm. The amount of the fine particles is more preferably from 1 to 10 wt %, and particularly preferably from 1 to 5 wt %.

Alternatively, these secondary particles are preferably mixed with from 1 to 30 wt % of a fine ceramic powder having a size of from about 0.1 to 2 μm. The amount of the fine ceramic powder is more preferably from 1 to 10 wt %, and more preferably from 1 to 5 wt %.

In these preferred embodiments, the fine particles or the fine ceramic powder will serve as a binder for the secondary particles made by granulation, thus contributing to the formation of a stronger ceramic material. If the amount of the fine particles or the fine ceramic powder is too large, they will shut the micropores of the resulting sinter.

The high molecular weight material used in the present invention must have properties that it forms a gel under certain conditions, such as heating, addition of an additive or the like, or its viscosity is increased under certain conditions. Any high molecular weight materials can be used if they satisfy the above requirements.

Upon heating, a solution of certain high molecular weight materials such as methyl cellulose becomes more viscous as the temperature rises and gels reversibly at a certain temperature. Some high molecular weight materials such as polyvinyl alcohol gel reversibly when a certain additive such as boric acid or borax is added. Both types of high molecular weight materials can be used in the process of the present invention.

In one embodiment of the present invention, a solution or a fluid gel of the high molecular weight materials described above is mixed with the ceramic powder and the mixture is stirred to entrain air, thereby forming a slurry containing spherical air bubbles. When the slurry is poured into a mold and increased in viscosity or allowed to gel followed by drying while maintaining the air bubbles, the bubbles will shrink substantially isotropically to provide a dried body of high strength that is free from cracking and other defects and that has spherical macropores.

The high molecular weight material used in the present invention need not form gel. When a high molecular weight material which does not form gel is used in this embodiment, for example, a solution of the material is mixed with the starting ceramic powder and the mixture then stirred to entrain air bubbles in the mixture. The resulting mixture containing bubbles (preferably having a viscosity of from 10 to 160 poise, more preferably from 60 to 100 poise) is poured into a mold and, after increasing the viscosity, the cast product is dried to provide a dried body of the present invention.

In another embodiment of the present invention, the solution or fluid gel of a high molecular weight material is first stirred to entrain air and then mixed with the starting ceramic powder.

In still another embodiment of the present invention, the powderous high molecular weight material and the ceramic powder are mixed, and then a dispersion medium (such as water) is added thereto to form a slurry, followed by being stirred to entrain air bubbles into the slurry.

The high molecular weight material to be used in the process of the present invention is preferably water soluble since water is generally used as a dispersion medium for the starting ceramic powder. If other dispersion media are to be used, high molecular weight materials that are soluble in those media may be selected. Examples of the water-soluble high molecular weight materials that can be used include methyl cellulose, carboxymethyl cellulose, polyvinyl alcohol, polyacrylic acid, polyacrylamide, polyvinyl pyrrolidone, Curdlan, etc.

Other combinations of dispersion media and high molecular weight materials, such as ethanol, methanol and isopropanol with hydroxypropylcellulose, may be used in the present invention. The solvent for the solution or fluid gel of the high molecular weight material may be water as well as those for the dispersion medium.

The amount of the high molecular weight material used will vary with the type but it is generally preferred to incorporate it in an amount of from 0.5 to 10 wt % of the slurry. The preferred range is from 0.2 to 2 wt %, more preferably from 0.5 to 1 wt %, for methyl cellulose, and from 5 to 10 wt % for polyvinyl alcohol. If excessively large amounts of high molecular weight material are used, not only is it necessary to perform degreasing before firing but also sinterability is deteriorated. If the amount of the high molecular weight material used is too small, air bubbles will not be retained in the slurry.

The porous dried body prepared by the process of the present invention comprises ceramic particles which are bound together with the high molecular weight material to provide a strength that withstands subsequent cutting operations. Therefore, the dried body produced by the process of the present invention may be immediately subjected to cutting without calcination.

The size and quantity of the air bubbles incorporated in the fluid gel or solution can be controlled by adjusting the intensity and time of stirring as well as the efficiency of the stirrer used. A uniform pore size of 3 mm or less can be easily obtained. In general, higher speed of stirring, higher efficiency of the stirrer and longer time of stirring each will provide a larger amount of air bubbles entrained.

The dried body, which is optionally subjected to cutting, may be fired to form a sinter of the present invention. The resulting sinter contains not only the spherical macropores formed from the entrained air bubbles but also three-dimensionally communicating micropores that comprise interstices between the spherical secondary particles in the starting ceramic material. At a porosity of less than 40%, the macropores derived from the bubbles of confined air are closed and hence do not communicate with each other. On the other hand, the micropores are open and permit slow passage of low viscosity fluids. If the porosity is 40% or more, open macropores will be established. The porosity of the sinter of the present invention is not particularly limited but is preferably from 25 to 75%.

The pore size of the macropore in the sinter of the present invention varies widely depending on the use thereof. For example, the pore size of the macropore is preferably 100 μm or more for bone prostheses. The pore size of the micropore in the sinter of the present invention depends on the particle size of the starting ceramic powder, because the micropores are constituted from gaps between the particles of the starting ceramic powder.

The pore size of the macropore in the sinter is substantially the same as the size of the air bubbles in the slurry to be cast in a mold.

The process of the present invention is applicable to various kinds of ceramics including calcium phosphate series, alumina series, silica series and zirconia series ceramics, and it can be used in the manufacture of various products including artificial biomaterials, packings for liquid chromatography, catalyst supports, electrical and electronic materials, nuclear reactor materials, ceramic heating elements, etc.

The following examples are provided for the purpose of further illustrating the present invention but are in no way to be taken as limiting. Unless specifically indicated, all parts, percents, etc., are by weight, and all procedures were operated at room temperature.

EXAMPLE 1

After charging 150 g of water into a 500 ml beaker, 2.7 g of methyl cellulose (polymerization degree: 4,000 cps, made by Wako Pure Chemical Co., Ltd.) was added and mixed for 3 minutes with a hand mixer to prepare an aqueous solution of methyl cellulose. The beaker was placed in a thermostatic chamber at 60° C. and the temperature of the contents of the beaker was raised to 40° C. with stirring, and the system was then stirred for an additional 30 seconds to obtain a fluid gel.

A hydroxyapatite slurry synthesized by a known wet method was spray dried to form granules having an average particle size of 12 $\mu$m. The granules were pulverized with a jet mill to prepare a hydroxyapatite powder containing spherical particles of hydroxyapatite having an average particle size of 10 $\mu$m and fine particles of hydroxyapatite having an average particle size of 1 $\mu$m.

The beaker was taken out of the thermostatic chamber and 50 g of the above prepared spherical hydroxyapatite particles was slowly added and mixed little by little into the contents of the beaker. After viscosity measurement (by using Rion Viscometer VT-04, made by Rion Company Ltd.),.the mixture was poured into a 200-ml glass beaker. After gelling and drying the contents of the beaker in a dryer at 90° C. for 24 hours, the contents were recovered from the beaker, cut into cubes (dimension: 45×30×10.5 mm) with a hand saw and degreased and fired according to the following schedule to obtain a sinter (MC1): heating from room temperature to 600° C. at a rate of 50° C./h, further heating to 1,200° C. at a rate of 100° C./h, firing at 1,200° C. for 4 hours, cooling down to 600° C. at a rate of 50° C./h, holding at 600° C. for 4 hours, and further cooling down to room temperature at a rate of 100° C./h.

Two additional samples (MC2 and MC3) of sinter were produced by the same manner as above except that the aqueous solution of methyl cellulose was heated to 45° C. or 50° C., respectively.

The dimension of the resulting sinters was 30×20×7 mm.

Figure 2:

Micrographs of the sinters MC1 and MC2 are shown in FIGS. 1 and 2, respectively.

Measurements were conducted on each sinter sample for porosity, three-point bending strength and linear shrinkage. The results are shown in Table 1 below.

TABLE 1

| Sample No. | Temperature of methyl cellulose solution (°C.) | Viscosity of methyl cellulose solution (poise) | Porosity (%) | Strength (kg/cm$^2$) | Linear shrinkage (%) |
|---|---|---|---|---|---|
| MC1 | 40 | 60 | 54.1 | 60.2 | 68.1 |
| MC2 | 45 | 50 | 53.8 | 60.3 | 68.8 |
| MC3 | 50 | 20 | 50.7 | 52.4 | 68.4 |

EXAMPLE 2

A 1,000-ml beaker was charged with 450 g of water and 8.1 g of methyl cellulose (polymerization degree 4,000, made by Wako Pure Chemical Co., Ltd.). The ingredients were stirred with a hand mixer to dissolve the methyl cellulose completely in the water to produce a foam. When a meringue-like product formed, 50 g of the spherical hydroxapatite particles prepared in Example 1 were added and well mixed to form a homogeneous slurry. The slurry was poured into four 200-ml beakers, respectively, and the beakers were placed in a dryer where they were held at 90° C. for 3 hours to form a gel, and further placed in the dryer for 48 hours to dry the gel. After drying, the dried body was treated as in Example 1 to make a sinter and its porosity and three-point bending strength were measured. The porosity was 57.2% and the flexural strength was 44.2 kg/cm$^2$.

EXAMPLE 3

Figure 3:
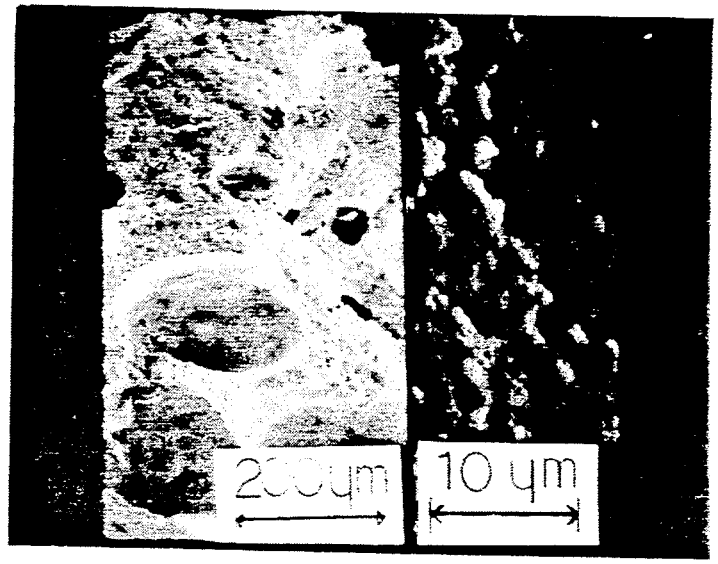
FIG. 3 shows a micrograph of the sinter obtained in Example 3.

Two grams of carboxymethyl cellulose (polymerization degree: 300 to 500, made by Serva Feinbiochemica GmbH & C) was mixed well with 100 g of spherical particles of partially stabilized zirconia having 3 mol % of yttria dissolved therein. To the mixture, 100 g of water was added and the mixture was stirred well with a hand mixer to form a slurry of ceramic zirconia containing air bubbles. This slurry was poured into a 300-ml beaker, and increased in viscosity and dried with a dryer at 90° C. for 24 hours. The dried product was cut into cubes with a hand saw and fired according to the following schedule to obtain a sinter: heating to 1,550° C. at a rate of 300° C./h, hold at 1,550° C. for 2 hours, and cooling down to room temperature at a rate of 200° C./h. A micrograph of the sinter is shown in FIG. 3. The porosity and three-point bending strength of the resulting sinter was measured.

The ceramic sinter was a porous material having open macropores and its average porosity and bending strength were 43.8% and 688 kg/cm$^2$, respectively.

EXAMPLE 4

Figure 4:
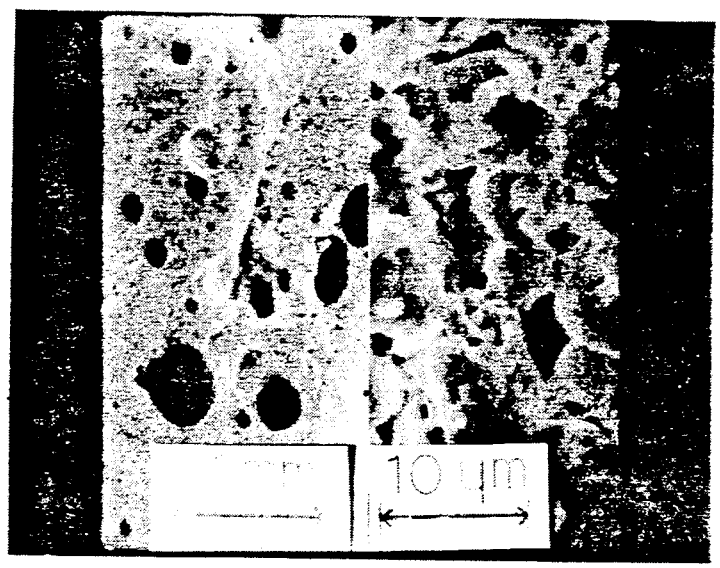
FIG. 4 shows a micrograph of the sinter obtained in Example 4.

150 g of a 7% aqueous solution of polyvinyl alcohol (polymerization degree: 2,000, made by Wako Pure Chemical Co., Ltd.) and 100 g of a 5% aqueous solution of boric acid each was charged into separate vessels and heated on a water bath at 80° C. When the temperature of both solutions reached 70° C. or higher, they were mixed together with stirring and the mixture was cooled with continued stirring. When the mixed solution became a fluid gel containing air bubbles and was somewhat turbid, the stirring was stopped and the solution was mixed with 120 g of the spherical hydroxyapatite particles prepared in Example 1. The mixture was put into a 300 ml beaker, dried to gel in a dryer by heating at 50° C. for 24 hours and further dried in a dryer at 90° C. for 24 hours. Thereafter, the dried product was shaped, degreased and fired as in Example 1 to produce a porous ceramic sinter containing spherical pores which had an average porosity of 54.1% and an average flexural strength of 41 kg/cm$^2$. A micrograph of the sinter is shown in FIG. 4.

EXAMPLE 5

A hydroxyapatite slurry synthesized by a known wet process was spray dried to form particles having an average size of 12 $\mu$m. Part of these spherical particles of hydoxyapatite was pulverized with a ball mill to produce fine particles having an average particle size of 1 $\mu$m.

Two grams of methyl cellulose were added to 150 g of water and dissolved with stirring to form an aqueous solution containing air bubbles. To this solution, 45 g of the particles having an average size of 12 μm and 5 g of the fine particles produced as above were added and the resulting dispersion mixed thoroughly.

The resulting mixture was poured into a 300 ml beaker, which was then placed in a dryer, where it was held at 80° C. for 36 hours to gel and dry the contents. The resulting dried product was processed as in Example 1 to produce a sinter. The sinter had an average porosity of 57.2% and an average bending strength of 48.2 kg/cm$^2$.

EXAMPLE 6

1.5 g of methylcellulose was dissolved in 100 g of water, and stirred to entrain air bubbles. 50 g of powder of partially stabilized zirconia solid-dissolved therein 3 mol % of yttria, which was produced by co-precipitation followed by filtering, was added to the methylcellulose solution and stirred. The mixture was poured into a 200-ml beaker and placed in a dryer at 80° C. for 24 hours to be gelled and dried. The dried product obtained was processed and fired in the same manner as in Example 3 to obtain a porous zirconia ceramic sinter. The sinter had an average porosity of 58.2% and an average bending strength of 321.7 kg/cm$^2$.

The porous ceramic sinter of the present invention has macropores of a uniform size and three-dimensionally communicating micropores. Because of this unique porous structure, the sinter not only has high strength but also has good cutting properties and can advantageously be used as a material to yield various products, including artificial bio-materials, packing for liquid chromatography, catalyst supports, electrical and electronic materials, nuclear reactor materials, ceramic heating elements, etc.

According to the process of the present invention, the slurry being dried will shrink substantially isotropically and a desired porous ceramic sinter and dried body can be easily produced without experiencing cracking or any other problems in the drying.

Further, in the process of the present invention, the size and quantity of air bubbles to be incorporated in the fluid gel or viscous solution can be controlled by adjusting the intensity of stirring and macropores of a uniform size not exceeding 3 mm can be easily obtained. It is also possible to fabricate a porous sinter of a comparatively complex shape having macropores with a size not exceeding 1 mm.

The ceramic particles in the dried body are bound together by the high molecular weight material, so it has a sufficient strength to withstand subsequent cutting operations and can be machined as such by means of cutting without calcination.

In a preferred embodiment of the process of the present invention, the secondary particles of a starting ceramic powder are used in combination with fine particles of the same powder, and this contributes to the production of a ceramic sinter of even higher strength.

While the invention has been described in detail and with reference to specific embodiments thereof, it will be apparent to one skilled in the art that various changes and modifications can be made therein without departing from the spirit and scope thereof.

What is claimed is:

1. A process for producing a porous ceramic sinter which comprises: mixing a ceramic powder with a high molecular weight material; mixing the mixture with a dispersion medium; stirring the mixture to entrain air bubbles in the mixture to thereby yield a slurry; casting the resulting slurry comprising the ceramic powder, the high molecular weight material, the dispersion medium and the air bubbles into a mold; increasing the viscosity of the case product while maintaining the air bubbles; drying the viscous cast product; and firing the dried body, wherein said high molecular weight material is water soluble high molecular weight carboxymethyl cellulose which is incorporated in an amount of from 0.5 to 10 wt % of said slurry.

2. A process for producing a porous ceramic sinter which comprises: mixing a ceramic powder with an aqueous solution or an aqueous fluid gel of a high molecular weight material into which air bubbles have been entrained by stirring to yield a slurry; casting the resulting slurry into a mold; allowing the cast product to gel while maintaining the air bubbles; drying the gelled cast product; and firing the dried body, wherein said high molecular weight material is water soluble high molecular weight methyl cellulose.

3. A process for producing a porous ceramic sinter as claimed in claim 2 wherein:
   the aqueous fluid gel is used and the aqueous fluid gel is formed by stirring the methyl cellulose in water to completely dissolve the methyl cellulose;
   the ceramic powder comprises spherical particles of hydroxyapatite having an average particle size of 10 μm and fine particles of hydroxyapatite having an average particle size of 1 μm;
   the slurry is homogeneous;
   the cast product is allowed to gel by heating while maintaining the air bubbles; and
   the drying of the gelled cast product is a further drying to form a dry gel.

4. A process for producing a porous ceramic sinter as claimed in claim 2 wherein:
   the aqueous solution is used and it is formed by dissolving the methyl cellulose in water with stirring to form the aqueous solution in which the air bubbles have been entrained by the stirring;
   the ceramic powder comprises hydroxyapatite particles having an average size of 12 μm and hydroxyapatite fine particles having an average particle size of 1 μm; and
   the allowing of the cast product to gel is by drying.

5. A process for producing a porous ceramic sinter as claimed in claim 2, wherein the amount of methyl cellulose is from 0.5 to 10 wt % of the slurry.

6. A process for producing a porous ceramic sinter as claimed in claim 2, wherein the amount of methyl cellulose is from 0.2 to 2 wt % of the slurry.

7. A process for producing a porous ceramic sinter as claimed in claim 2, wherein the amount of methyl cellulose is from 0.5 to 1 wt % of the slurry.

8. A process for producing a porous ceramic sinter as claimed in claim 2, wherein said ceramic powder comprises spherical secondary particles having an average particle size of from about 10 to 100 μm.

9. A process for producing a porous ceramic sinter as claimed in claim 6, wherein said spherical secondary particles are pulverized to such an extent that fine particles with a size of from about 0.1 to 2 μm form in an amount sufficient to serve as a binder for the secondary particles which have been made by granulation.

10. A process for producing a porous ceramic sinter as claimed in claim 2, wherein said ceramic powder is hydroxyapatite particles.

11. A process for producing a porous ceramic sinter which comprises: mixing a ceramic powder with an aqueous solution or an aqueous fluid gel of a high-molecular weight material; stirring the mixture to entrain air bubbles in the mixture to thereby yield a slurry; casting the resulting slurry into a mold; allowing the cast product to gel due to the addition of a material selected from the group consisting of boric acid and borax while maintaining the air bubbles; drying the gelled cast product; and firing the dried body, wherein said high molecular weight material is water soluble high molecular weight polyvinyl alcohol.

12. A process for producing a porous ceramic sinter which comprises: dissolving methyl cellulose in water and stirring the dissolved methyl cellulose in water to entrain air bubbles therein; adding powdered partially stabilized zirconia solid having dissolved therein yttria to the methyl cellulose solution and stirring the resulting methyl cellulose solution containing the partially stabilized zinconia; drying the resulting product which results in gelling the resulting product; and firing the resulting gelled and dried product.

* * * * *